(12) United States Patent
Schima et al.

(10) Patent No.: US 8,303,482 B2
(45) Date of Patent: Nov. 6, 2012

(54) METHOD AND SYSTEM FOR PHYSIOLOGIC CONTROL OF A BLOOD PUMP

(75) Inventors: Heinrich Schima, Vienna (AT); Michael Vollkron, Vienna (AT); Gino Morello, Leonia, NJ (US); Robert Benkowski, Fort Worth, TX (US)

(73) Assignee: Micromed, Houston, TX (US)

( * ) Notice: Subject to any disclaimer, the term of this patent is extended or adjusted under 35 U.S.C. 154(b) by 1060 days.

(21) Appl. No.: 11/663,115

(22) PCT Filed: Sep. 7, 2005

(86) PCT No.: PCT/US2005/031880
§ 371 (c)(1),
(2), (4) Date: Sep. 9, 2008

(87) PCT Pub. No.: WO2006/029216
PCT Pub. Date: Mar. 16, 2006

(65) Prior Publication Data
US 2009/0005632 A1 Jan. 1, 2009

Related U.S. Application Data

(60) Provisional application No. 60/522,260, filed on Sep. 7, 2004.

(51) Int. Cl.
*A61N 1/362* (2006.01)
*A61M 1/10* (2006.01)
(52) U.S. Cl. ............ 600/17; 600/16; 623/3.1; 623/3.28; 623/3.3; 415/900
(58) Field of Classification Search .................... 600/16, 600/17; 623/3.28, 3.1, 3.3; 415/900
See application file for complete search history.

(56) References Cited

U.S. PATENT DOCUMENTS

| | | | |
|---|---|---|---|
| 4,221,543 | A | 9/1980 | Cosentino et al. |
| 4,363,609 | A | 12/1982 | Cosentino et al. |
| 4,657,529 | A | 4/1987 | Prince et al. |
| 4,763,032 | A | 8/1988 | Bramm et al. |
| 4,944,748 | A | 7/1990 | Bramm et al. |
| 5,078,741 | A | 1/1992 | Bramm et al. |
| 5,326,344 | A | 7/1994 | Bramm et al. |
| 5,385,581 | A | 1/1995 | Bramm et al. |
| 5,536,237 | A | 7/1996 | Prince et al. |

(Continued)

FOREIGN PATENT DOCUMENTS
EP 1354606 10/2003
(Continued)

OTHER PUBLICATIONS

International Preliminary Report on Patentability for International Patent Application No. PCT/US2005/031880.

(Continued)

*Primary Examiner* — Niketa Patel
*Assistant Examiner* — William Levicky
(74) *Attorney, Agent, or Firm* — Sutton McAughan Deaver PLLC

(57) ABSTRACT

A physiologic control system and method for controlling a blood pump system such as a VAD system. The pump system includes, for example, a blood pump and a controller for controlling the pump. The system may further include a flow measurement device. A desired peak to peak flow amplitude is determined, and then adjusted in response to various system parameters either manually or automatically by the system.

14 Claims, 15 Drawing Sheets

U.S. PATENT DOCUMENTS

| | | |
|---|---|---|
| 5,863,421 A | 1/1999 | Peter, Jr. et al. |
| 5,888,242 A | 3/1999 | Antaki et al. |
| 6,066,086 A * | 5/2000 | Antaki et al. .................. 600/17 |
| 6,183,412 B1 | 2/2001 | Benkowski et al. |
| 6,274,034 B1 | 8/2001 | Nikaido et al. |
| 6,277,272 B1 | 8/2001 | Nikaido et al. |
| 6,454,697 B1 | 9/2002 | Wang |
| 6,551,513 B2 | 4/2003 | Nikaido et al. |
| 6,582,604 B2 | 6/2003 | Nikaido et al. |
| 6,605,032 B2 | 8/2003 | Benkowski et al. |
| 6,623,420 B2 | 9/2003 | Reich et al. |
| 6,817,836 B2 | 11/2004 | Nose et al. |
| 6,884,210 B2 | 4/2005 | Nose et al. |
| 7,172,570 B2 | 2/2007 | Cavalcanti et al. |
| 7,284,956 B2 | 10/2007 | Nose et al. |
| 2002/0150476 A1 | 10/2002 | Lucke et al. |
| 2003/0069465 A1 | 4/2003 | Benkowski et al. |
| 2003/0163020 A1 | 8/2003 | Frazier |
| 2003/0199727 A1 | 10/2003 | Burke et al. |

FOREIGN PATENT DOCUMENTS

| | | |
|---|---|---|
| WO | 2004002552 | 1/2004 |

OTHER PUBLICATIONS

International Search Report for International Patent Application No. PCT/US2005/031880.

Written Opinion for International Patent Application No. PCT/US2005/031880.

Supplementary Partial European Search Report for European Application No. 05795357.2.

* cited by examiner

FIG. 5A. Constant Speed

| Control | Speed limit/alarm | | Power | Flow | | Suction | Suction Detection |
|---|---|---|---|---|---|---|---|
| Variable | Min | Max | Max | Min | Max | Detection | Response |
| enter Speed | 7.5k | | 15W | enter min | | Enabled/Disabled | Enabled/Disabled |

FIG. 5B Nominal Flow

| Control | Speed limit/alarm | | Power | Flow | | Suction | Suction Detection |
|---|---|---|---|---|---|---|---|
| Variable | Min | Max | Max | Min | Max | Detection | Response |
| enter Flow | 8.0k | 11.0k | 8+Flow * 1.5 | Flow * .75 | | Enabled | Enabled |

FIG. 5C. Constant waviness

| Control | Speed limit/alarm | | Power | Flow | | Suction | Suction Detection |
|---|---|---|---|---|---|---|---|
| Variable | Min | Max | Max | Min | Max | Detection | Response |
| P2P = 4 | 8.0k | 11.0k | 8+Flow * 1.5 | enter min | | Enabled | Enabled |

FIG. 5D Maximize Flow - waviness (P2P)

| Control | Speed limit/alarm | | Power | Flow | | Suction | Allow Flow |
|---|---|---|---|---|---|---|---|
| Variable | Min | Max | Max | Min | Max | Detection/Response | Below Baseline** |
| P2P = 2*** | 9.0k | 12.0k | 18 | imported | | Enabled/Enabled | Enabled/Disabled |

FIG. 5E Maximize Flow - dQ/dN (diminishing returns)

| Control | Speed limit/alarm | | Power | Flow | | Suction | Allow Flow |
|---|---|---|---|---|---|---|---|
| Variable | Min | Max | Max | Min | Max | Detection/Response | Below Baseline** |
| dQ/dN | 9.0k | 12.0k | 18 | imported | | Enabled/Enabled | Enabled/Disabled |

METHOD AND SYSTEM FOR PHYSIOLOGIC CONTROL OF A BLOOD PUMP

CROSS-REFERENCE TO RELATED APPLICATION

This application claims priority to U.S. Provisional Application Ser. No. 60/522,260, filed on Sep. 7, 2004, which is incorporated by reference.

BACKGROUND

This application relates generally to pump systems, and more specifically, to a method and system for physiologic control of blood pumps.

Generally, blood pump systems are employed in either of two circumstances. First a blood pump may completely replace a human heart that is not functioning properly, or second, a blood pump may boost blood circulation in patients whose heart is still functioning although pumping at an inadequate rate. The blood pump may be external, partially implanted or completely implanted.

For example, U.S. Pat. No. 6,183,412, which is commonly assigned and incorporated herein by reference in its entirety, discloses a ventricle assist device (VAD) commercially referred to as the "DeBakey VAD®." The VAD is a miniaturized continuous axial-flow pump designed to provide additional blood flow to patients who suffer from heart disease. The device is attached between the apex of the left ventricle and the aorta.

Known blood pump systems typically are controlled in an open loop fashion where a predetermined speed is set and the flow rate varies according to the pressure differential across the pump. The pump itself may be controlled in a closed loop fashion, wherein the actual pump speed is fed back to a motor controller that compares the actual speed to the desired predetermined speed proportional to some measured physiologic parameter and adjusts the pump accordingly. However, prior art devices using closed loop control systems which vary the pump speed in response to a monitored physiologic or pump parameter have largely been unsatisfactory.

The present invention addresses shortcomings associated with the prior art.

SUMMARY OF THE INVENTION

Aspects of the present invention concern a physiologic control system and method for controlling a blood pump system such as a VAD system. The pump system includes, for example, a blood pump and a controller for controlling the pump. The system may further include a flow measurement device. Various control schemes are disclosed, including controlling the pump to achieve one or more of a desired speed, flow rate, or flow pulsatility. Additionally, various methods for determining maximal flow (the maximum flow that can be achieved for the patient while maintaining certain parameters or within certain boundaries) are disclosed.

In certain exemplary embodiments in accordance with the teachings of the present disclosure, the desired peak-to-peak ("P2P") flow amplitude ("dP2PFA") of the control system is modified, either manually by the user or clinician or automatically by the system. If this adaptation of dP2PFA is done automatically by the system, it may be based on the effectiveness of a temporary speed change on flow, and such speed change can be done either by a temporary speed increase or a temporary speed decrease. This adaptation may also be done in response to the power increase at the temporary speed change.

In further exemplary embodiments, if at a given temporary speed increase the flow does not increase for more than a given amount, or if the increase requires a percentage power increase over a given level relating to flow increase, or if dP2PFA decreases for more than a certain amount at such speed increase; and where dP2PFA is decreased, if at a given speed increase flow does increase for more than a given amount and at the same time the percentage power does not increase over a given level and where at the same time the dP2PFA increases for more than a given amount; or where at a temporary speed decrease the system reactions inversely in the same sense. The given amounts for change can be modified by the user, which allows a balancing between elevated pumping and reduction of power and suction risk. Such adjustment may be be implemented via a user interface, which allows the user to select between various degrees of enhanced support versus energy optimized performance.

Alternatively, where the lines of discrimination may be described with absolute numbers of power increase instead of percentage description, and/or with percentage numbers of flow change instead of absolute numbers. Moreover, instead of straight lines of discrimination, a nonlinear function (such for example a squareroot function) may be used. Instead of a binary decision on increase or decrease of dP2PFA or a decision between increase, decrease and no change, a decision function is used, which gives a value of increase depending on the deviation distance of the discrimination, and in which that function is either defined analytically or via a fuzzy logic set.

BRIEF DESCRIPTION OF THE DRAWINGS

Other objects and advantages of the invention will become apparent upon reading the following detailed description and upon reference to the drawings in which:

FIGS. 5A-5E illustrate various parameters for exemplary pump control modes in accordance with embodiments of the invention.

Figure 1:
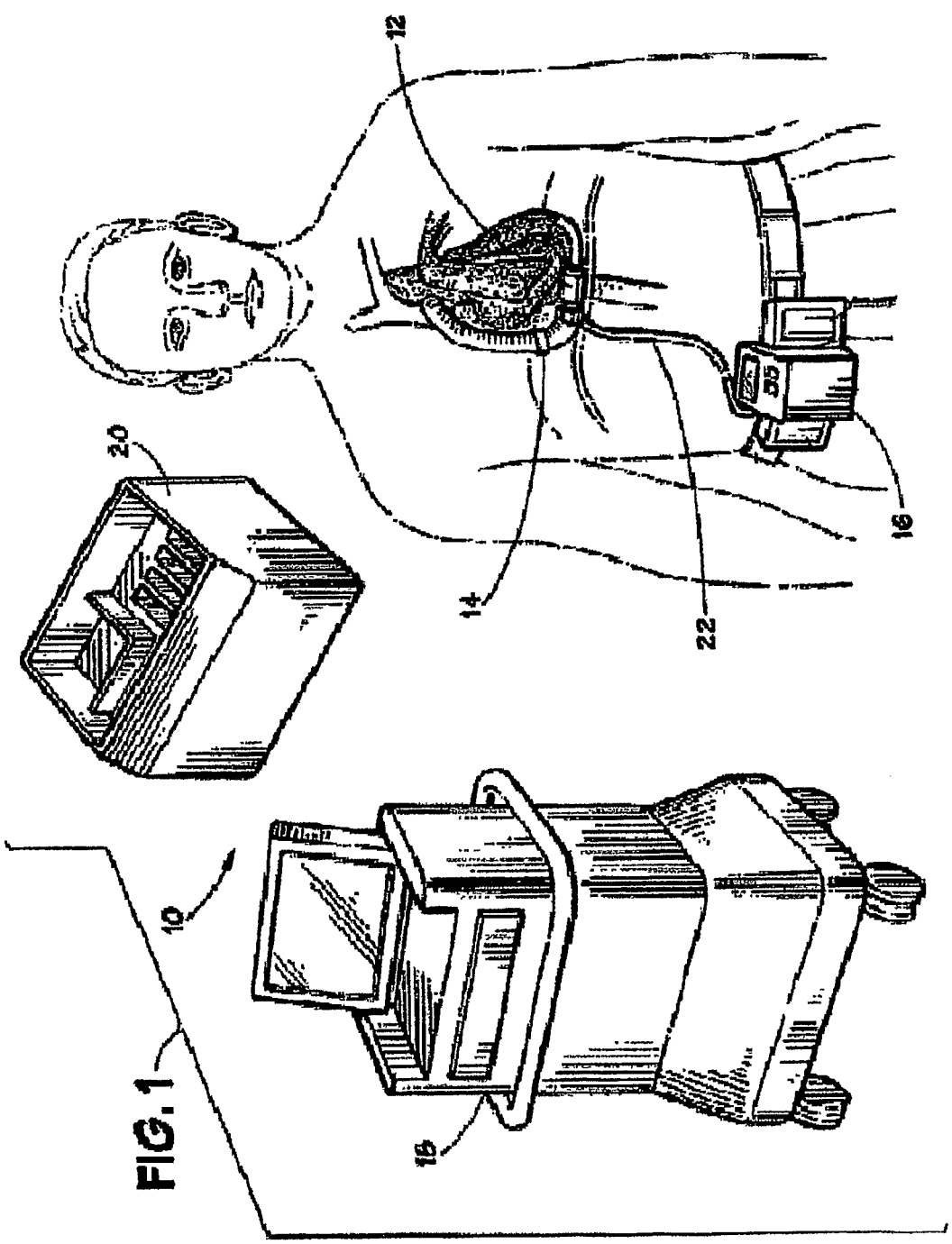
FIG. 1 schematically illustrates various components of a blood pump system in accordance with embodiments of the present invention.

While the invention is susceptible to various modifications and alternative forms, is specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning to the figures, FIG. 1 illustrates a ventricular assist device (VAD) system 10 such as disclosed in U.S. Pat. No. 6,183,412, which is commonly assigned and incorporated herein by reference in its entirety. The VAD system 10 includes components designed for implantation within a human body and components external to the body. Implantable components include a rotary pump 12 and a flow sensor 14. The external components include is a portable controller module 16, a clinical data acquisition system (CDAS) 18, and a patient home support system (PHSS) 20. The implanted components are connected to the controller module 16 via a percutaneous cable 22.

Figure 2:
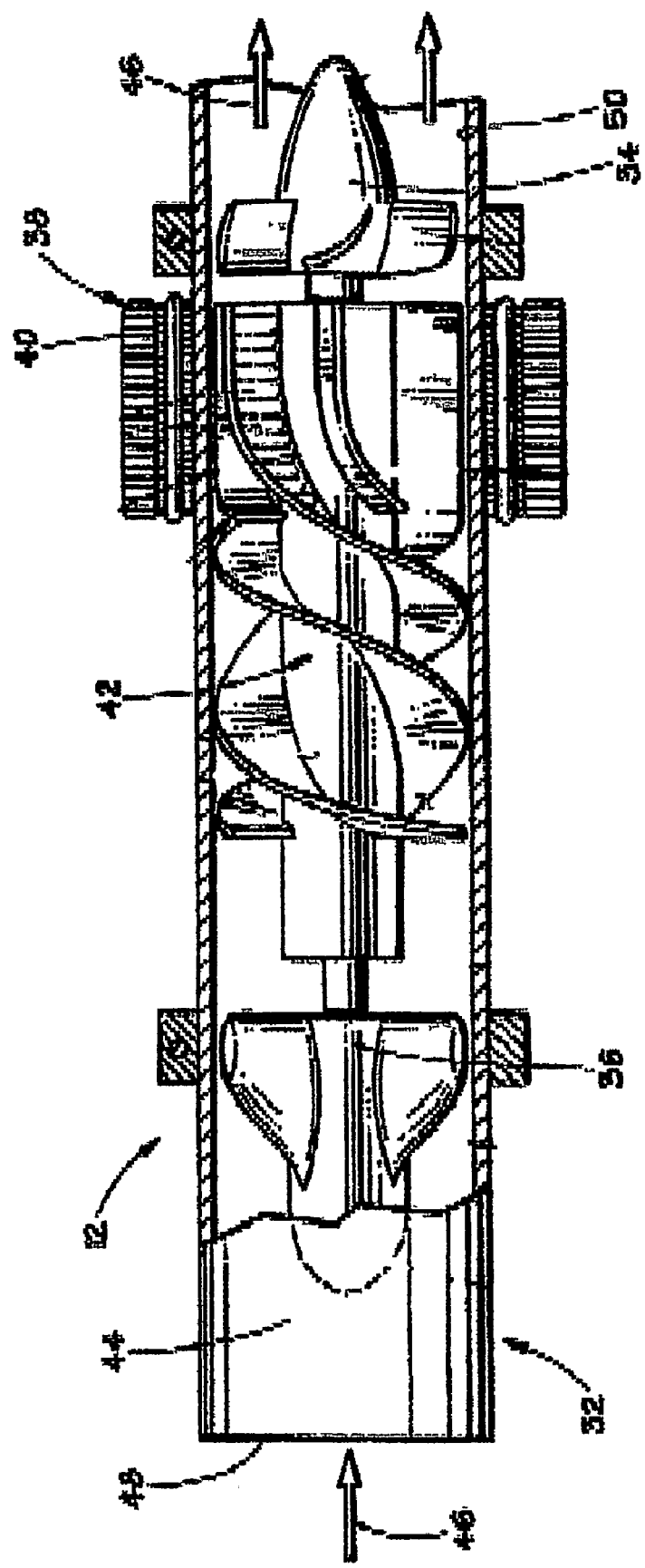
FIG. 2 is a cross-section view of an exemplary blood pump in accordance with embodiments of the present invention.

The VAD System 10 may incorporate a continuous-flow blood pump, such as the various embodiments of axial flow pumps disclosed in U.S. Pat. No. 5,527,159 or in U.S. Pat. No. 5,947,892, both of which are incorporated herein by reference in their entirety. An example of a blood pump suitable for use in an embodiment of the invention is illustrated in FIG. 2. The exemplary pump 12 includes a pump housing 32, a diffuser 34, a flow straightener 36, and a brushless DC motor 38, which includes a stator 40 and a rotor 42. The housing 32 includes a flow tube 44 having a blood flow path 46 therethrough, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotating magnetic field to produce rotary motion.

Figure 3:
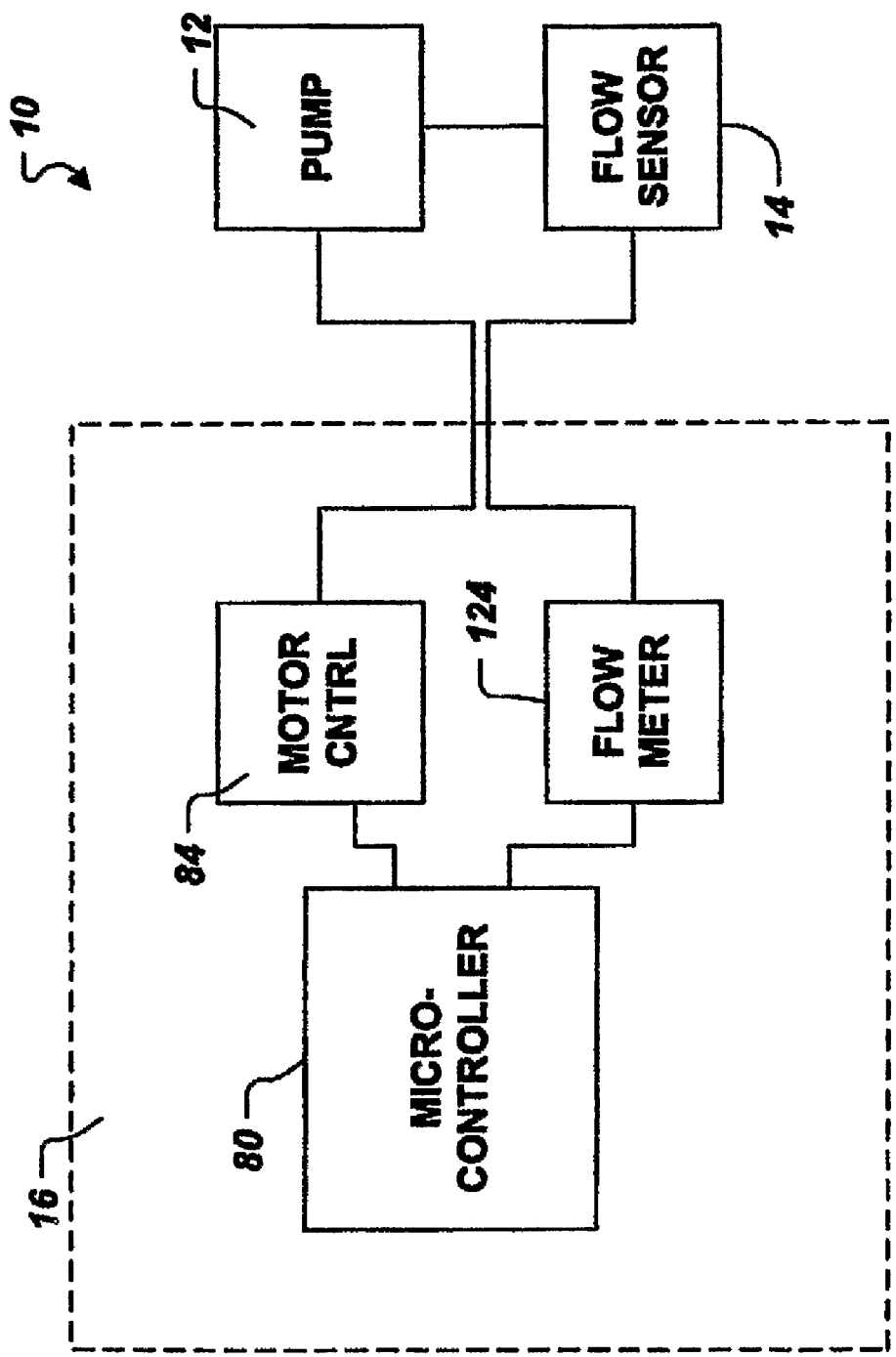
FIG. 3 is a block diagram illustrating aspects of a controller module in accordance with embodiments of the present invention.

FIG. 3 conceptually illustrates aspects of the pump system 10. More specifically, portions of the controller module 16 and the pump 12 are shown. The controller module 16 includes a processor, such as a microcontroller 80, which in one embodiment of the invention is a model PIC16C77 microcontroller manufactured by Microchip Technology. The microcontroller 80 includes a multiple channel analog to digital (A/D) converter, which receives indications of motor parameters from the motor controller 84. Thus, the controller module 16 may monitor parameters such as instantaneous motor current, the mean or RMS value of the motor current, and motor speed.

The embodiment shown in FIG. 3 further includes an integral flow meter 124. At least one flow sensor 14 is implanted down stream of the pump 12. Alternately, a flow sensor 14 may be integrated with the pump 12. The flow meter 124 is coupled between the implanted flow sensor 14 and the microcontroller 80. The flow meter 124 receives data from the flow sensor 14 and outputs flow rate data to the microcontroller 80, allowing the system to monitor instantaneous flow rate.

Since the implanted flow sensor 14 is coupled to the flow meter 124 of the controller module 16, a true measure of system performance (flow rate) is available for analysis, in addition to pump parameters such as motor speed and current (power). Further, since the flow meter 124 is an integral component of the controller module 16, flow rate may be displayed on the controller module display and flow rate data may be saved in the controller module's memory.

In exemplary embodiments of the invention, the motor controller 84 comprises a Fairchild Semiconductor ML4425 Motor Controller. The operation of the brushless DC motor 38 of the present invention requires that current be applied in a proper sequence to the stator windings 52 to create the rotating field. Two stator windings 52 have current applied to them at any one time, and by sequencing the current on and off to the respective stator windings 52, the rotating magnetic field is produced. In an embodiment of the invention, the motor controller 84 senses back electromotive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 of the brushless DC motor 38, a voltage is induced. The voltage will increase with rotor speed 42. It is possible to sense this voltage in one of the three stator windings 52 because only two of the motor's windings 52 are activated at any one time, to determine the rotor 42 position.

An alternative method of detecting the rotor 42 position relative to the stator 40 for providing the proper stator winding 52 excitation current sequence is to use a position sensor, such as a Hall effect sensor. Implementing aspects of the present invention using a motor with rotor position sensors, rather than a sensorless motor, would be a routine undertaking for one skilled in the art having the benefit of this disclosure. However, adding additional components, such as Hall effect sensors, requires additional space, which is limited in any implanted device application. Further, using a position detection device adds sources of system failures.

The actual pump speed is determined and fed back to the controller module 16, which compares the actual speed to a desired predetermined speed and adjusts the pump 12 accordingly. In accordance with certain embodiments of the invention, the pump 12 is controlled in a closed loop fashion wherein the desired pump speed is varied based on various physiologic factors.

U.S. Provisional Patent Application Nos. 60/346,555 and 60/319,318, filed on Jan. 8, 2002, and Jun. 14, 2002 respectively, both entitled "METHOD AND SYSTEM FOR DETECTING VENTRICULAR COLLAPSE," disclose methods of detecting ventricular collapse, or excess suction. U.S. Provisional Application No. 60/346,721, filed on Jan. 7, 2002, discloses physiologic pump control methods based on diastolic flow, among other things. The entire disclosures of these provisional applications are incorporated by reference herein.

Figure 4A:
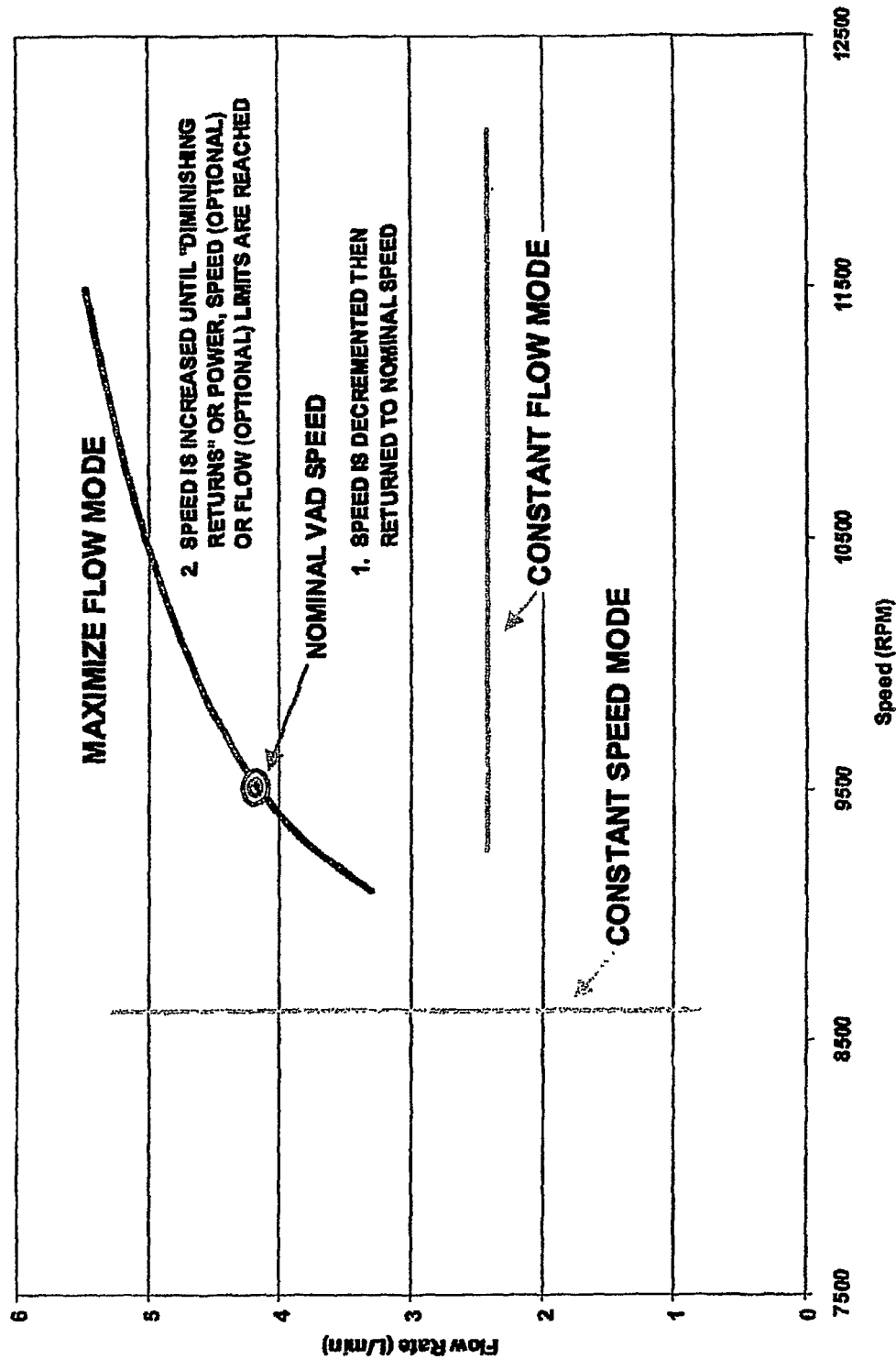
FIG. 4A is a chart illustrating three control modes in accordance with aspects of the present invention.

FIG. 4A illustrates three control modes in accordance with aspects of the present invention that employ suction detection and physiologic "triggers" as disclosed in the above-mentioned incorporated provisional applications: "constant speed," "constant flow" and "maximize, or maximal, flow." These control modes are shown via a plot of flow rate vs. pump speed. In the constant speed mode, the pump speed remains constant with changes in flow rate and in the constant flow mode, the flow rate remains constant as the speed varies. The constant speed mode is suitable, for example, intraoperatively, while weaning the patient off cardiopulmonary bypass, following surgery, and when the patient is discharged from the hospital. As noted above, the pump is operated at a fixed, predetermined speed. The speed may be optionally adjusted in response to suction events—i.e., the pump speed may be reduced in response to detected suction events. The nominal flow mode is suitable, for example, for patients in intensive care (ICU), recovery or during weaning from bypass.

The maximize, or maximal, flow mode is suitable, for example, during recovery or during exercise. With the maximize flow mode, the pump speed is periodically increased until a "diminishing returns" point is reached, and/or until another predetermined limit is reached (i.e. maximum power, maximum pump speed, etc.). In other words, the controller increases pump speed to a point at which an increase in pump speed no longer produces a corresponding increase in flow or a corresponding decrease in -to-peak amplitude. The maximize flow mode may be manually enabled by the patient, for instance, via a push button at the start of exercise, or it may be automatically triggered in response to a predetermined parameter.

Figure 4B:
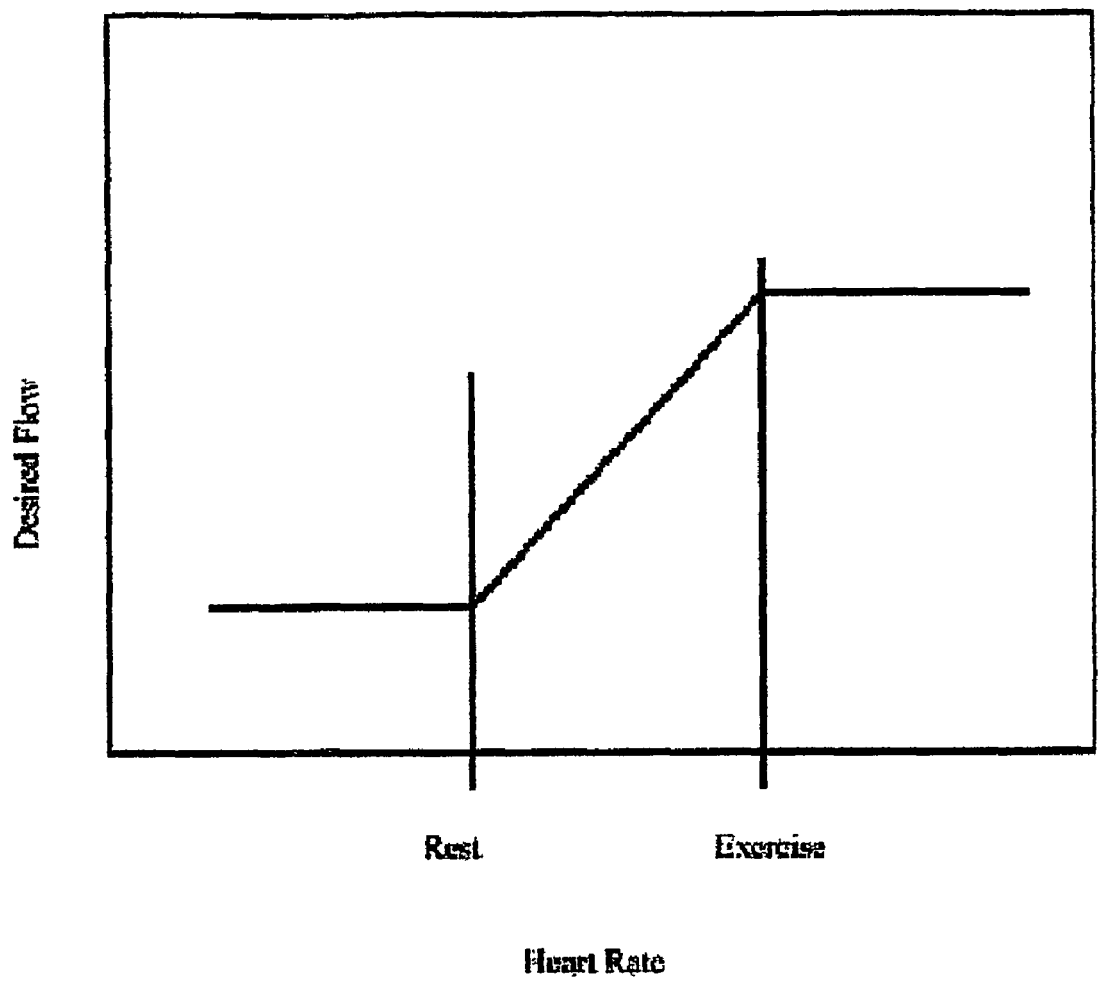
FIG. 4B is a chart illustrating a control mode where desired flow for the pump is proportional to a linear interpolation of the patients heart rate.
Figure 6A:
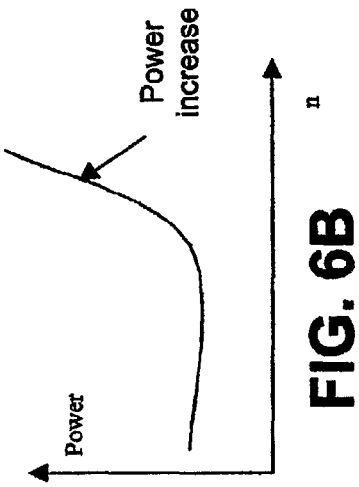
FIGS. 6A-6C illustrate peak-to-peak amplitude, power and speed regression curves.
Figure 6B:
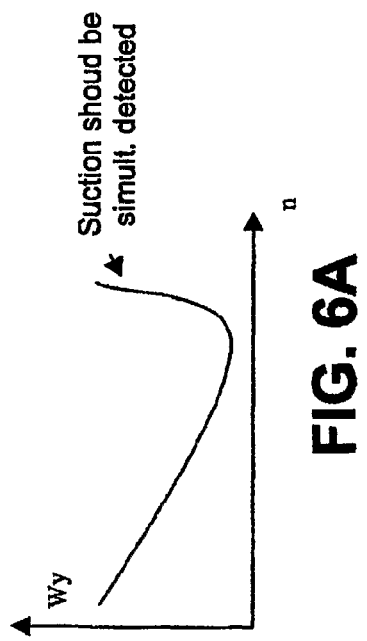
Figure 6C:
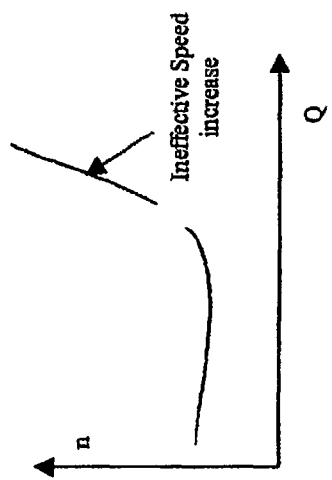

FIG. 4B shows a control mode in which the desired flow rate is generally proportional to a linear interpolation of heart rate. Desired rest and exercise flow rates are established, and in the illustrated mode, the desired flow rates do not go below or above these rates, respectively, regardless of the heart rate. Between the rest and exercise heart rates, the desired flow rate varies with heart rate.

FIG. 5 provides additional aspects of the constant speed, nominal flow and maximize flow, as well as a "constant peak-to-peak amplitude" mode. In some implementations, the physician may select which control mode is the most appropriate for the patient. The means to enable a true "physiologic" response is via a trigger—for example, diastolic flow or heart rate, or a combination of the two, as identified in the incorporated provisional applications. Alternatively, a manual trigger, such as an "exercise" button on the controller 16 may be used. The physician may selectively enable or disable the exercise button or the automatic triggers and may selectively decide if flow will be maximized by "diminishing returns" (change in flow for a given change in speed) or maximized by "minimal peak-to-peak amplitude" (the flow pulsatility, or peak-to-peak amplitude, decreases as pump speed is increased)

If the desired flow for the patient cannot be achieved (e.g. a boundary condition is reached such as maximum speed, maximum power), then pump speed is not adjusted further.

In other implementations, the control mode may be changed and the pump speed is reduced to achieve a desired peak-to-peak amplitude. In the control modes shown in FIG. 5, suction detection is either enabled or disabled. In other embodiments, varying levels of "ventricular unloading" are employed, assuming that the risk for suction is greatest with lower flow pulsatility.

Control parameters for each of the control modes are summarized and described in FIG. 5. For example, in the constant speed control mode shown in FIG. 5A, a clinician enters values for parameters shown in bold—the desired pump speed and the minimum flow rate. The values shown in regular type (not in bold) are default values that can be manually changed by the clinician. Additionally, the clinician enables or disables the "suction detection" and "suction detection response" parameters. If the suction response is enabled, upon detection of suction, the controller 16 activates a diagnostic alarm and reduces the pump speed by a predetermined amount and rate until suction disappears. For a suction-triggered speed reduction, the controller is programmed to wait a predetermined amount of time, then increase the speed by a predetermined amount and rate until the nominal speed is again achieved. If suction is detected again and the speed is reduced in response thereto (prior to achieving the nominal speed), the controller repeats the delay and subsequent speed increases. If suction is detected a third time with a corresponding speed reduction prior to achieving the nominal speed, the speed increase process repeats with a slower time period. A tone or other audible or visual signal is activated when the nominal speed is achieved. If the suction response is disabled, the diagnostic alarm is activated but no additional automatic responses are executed. If either the minimum speed or minimum flow is reached, the controller activates a diagnostic alarm and the speed is not reduced any further.

If the signal from the flow meter (or Flow Sensor Board, FSB) is not received or is corrupted, for example, a "bad flow signal" flag is set. In response to the detection of a poor flow signal, the controller activates a diagnostic alarm, the speed setting is not changed, and the FSB is reinitialized. If the flow signal is still considered unusable or invalid, the controller reinitializes the FSB periodically and suppresses the low flow alarm. If the flow signal returns (i.e. considered to be valid), the controller reverts back to the desired control mode, if the desired mode is other than the constant speed mode. Similarly, if a poor quality flow signal is received, the controller activates a diagnostic alarm, maintains the current speed setting and suppresses the low flow alarm. If the pump reaches the maximum power level, a diagnostic alarm is activated.

In the nominal flow mode shown in FIG. 5B, the desired flow rate is entered, and the maximum power and minimum flow parameters may be calculated based on the desired flow rate from the characteristic flow-pressure curves of the pump. The remaining parameters are default values that may be manually changed by the clinician. Upon detection of suction, the controller activates a diagnostic alarm and reduces speed by a predetermined amount and rate until the suction disappears. If the minimum speed or minimum flow level is reached, the controller activates a diagnostic alarm and does not reduce the speed any further.

For a suction-triggered speed reduction, the controller is programmed to wait a predetermined amount of time, then increase the speed by a predetermined amount and rate until the nominal flow is again achieved. If suction is detected again, and the speed is reduced in response thereto (prior to achieving the nominal flow), the controller repeats the delay and subsequent speed increases. If suction is detected a third time, with a corresponding speed reduction prior to achieving the nominal flow, the speed increase process repeats. A tone or other signal is activated when the nominal flow is achieved. If a bad flow signal or poor flow signal quality is received, the controller activates a diagnostic alarm and reverts to the constant speed control mode, with the speed set at "FSB fail speed"—typically 9000 RPM or the fail-safe speed, 8500 RPM. If the maximum power threshold setting is reached, the controller activates a diagnostic alarm and the speed is not allowed to increase further. If the maximum speed setting is reached, a diagnostic alarm is activated and the speed is not increased above the maximum speed value.

In the constant peak-to-peak amplitude mode shown in FIG. 5C, the minimum flow parameter is entered and control is based on the peak-to-peak amplitude ("P2P") of the flow signal. The remaining parameter values are defaults that can be manually changed by the clinician. If suction is detected the controller activates a diagnostic alarm and reduces speed by a predetermined amount and rate until the desired peak-to-peak amplitude is achieved. If the minimum speed or minimum flow setting is reached, the controller activates a diagnostic alarm and does not reduce speed any further.

In the event of a suction triggered speed reduction, the controller waits a predetermined amount of time, then increases speed by a predetermined amount and rate until the nominal peak-to-peak amplitude value is achieved. If, prior to reaching the nominal peak-to-peak amplitude, a suction triggered speed reduction occurs again, the speed increase is repeated after a predetermined time period. If a suction triggered speed reduction occurs a third time, the speed increase is repeated at a slower repetition rate. The controller activates a tone or other signal when the nominal peak-to-peak amplitude is achieved. If a "bad" flow signal or poor quality flow signal quality is received, the controller activates a diagnostic alarm and reverts back to the constant speed control mode, with the speed set at the FSB fail speed. If the maximum speed or power threshold levels are reached, the controller activates a diagnostic alarm and the speed is not increased further.

FIGS. 5D and 5E summarize the maximize flow algorithms based on peak-to-peak amplitude (pulsatility) or diminishing returns (change in flow vs. change in pump speed). The maximize flow mode is either enabled or disabled via settings on the CDAS 18. If the maximize flow mode is enabled, then either the peak-to-peak amplitude (P2P) or point of diminishing returns (dQ/dn) algorithm must be selected. Once the maximize flow mode is selected, the various triggers (e.g. diastolic flow, heartrate or exercise, for example) are individually enabled or disabled. In the illustrated embodiments, the maximize flow modes do not "branch" to any other modes; they may only return to the original control mode.

In the "maximize flow" control mode, based on peak-to-peak amplitude, the controller varies speed to maintain constant peak-to-peak amplitude of the flow signal. The peak-to-peak amplitude value may be dependent on the desired degree of ventricular unloading (for example, low, medium, high). If excess suction is detected, the controller activates a diagnostic alarm, reduces speed 200 RPM per second until suction disappears, waits 15 seconds, then attempts to servo to peak-to-peak amplitude.

The maximize flow mode based on diminishing returns is summarized in FIG. 5E. Speed is increased a predetermined amount and rate until the desired dQ/dn is achieved. Periodically, speed is increased to check for dQ/dn. The speed is then decreased, and if the dQ/dn does not vary, the controller continues to decrease the speed. In other words, the speed is always increased once, then decreased twice, then the controller waits a predetermined amount of time. If excess suction is detected, the controller activates a diagnostic alarm and reduces speed at a predetermined rate until the suction disappears. The controller then waits a predetermined amount of time, and then repeats the dQ/dn routine.

With either the peak-to-peak amplitude or diminishing return modes, if the minimum speed setting is reached, a diagnostic alarm is activated and the speed is not reduced further. If the minimum flow value is reached, the controller activates a diagnostic alarm, the speed is not reduced further, and the controller reverts back to original control mode. If the maximum speed or power value is reached, the controller activates a diagnostic alarm and does not increase the speed any further. If a bad flow signal is received, the controller activates a diagnostic alarm and reverts to the original control mode. The "baseline" flow is the mean flow prior to entering the maximize flow control mode. If the "Allow Flow Below Baseline" is enabled, the minimum flow threshold is a percentage of the baseline flow (baseline flow*predetermined percentage of baseline). The default setting is flow is "Not allowed below baseline".

In exemplary embodiments, the minimum speed limit is 7.5 kRPM, and the maximum speed limit is 12.5 kRPM. The hardware fail-safe speed is 8.5 kRPM. The bad flow signal or poor flow signal quality set speed ("FSB fail speed") is 9.0 kRPM. The controller module 16 indicates which mode is active, and also indicates whether peak-to-peak amplitude or "diminishing returns" is selected for the maximize flow algorithm and which triggers are active. The controller 16 further includes an "Exercise" button that is illuminated anytime the maximize flow algorithm is activated. In certain embodiments, the controller 16 is programmed such that the patient can defeat the maximize flow algorithm by holding the Exercise Button for a predetermined length of time, which also functions to defeat the automatic triggers for some predetermined time period.

Another control scheme in accordance with further exemplary aspects of the present invention is disclosed below. A desired flow rate, which is appropriate for the individual patient (e.g. to sustain a cardiac index of 2.0 Liter/min/m$^2$) is set by the clinician. This desired . flow can either be set constant for all conditions, or it can be optionally set to vary, for example, based on the heart rate of the patient to allow adaptation to exercise on an individual basis. As noted above, this physiologic "trigger" may alternatively be based on changes in the diastolic flow rate in addition to, or in place of, the patient's heart rate as described in U.S. Provisional Patent Application No. 60/346,721 filed on Jan. 7, 2002, the entire disclosure of which is incorporated by reference herein.

In embodiments using heart rate as a physiologic control parameter, the physician sets a typical "Heart rate at rest" for the patient, and a "Heart rate at Exercise," which the patient can achieve at advanced exercise, and he accordingly sets the "desired flow value at rest heart rate" and "desired flow value at exercise heart rate". The system will calculate internally a desired flow depending on the actual heart rate using a linearized, or polynomial, interpolation between rest and exercise flow rates corresponding to a linearized, or polynomial, interpolation between rest and exercise heart rate. Additionally, a "Minimal acceptable flow" is set. If the automatically controlled flow falls below that acceptable minimal flow for a predetermined amount of time, the system will switch to a safety mode based on constant speed. Finally, the physician may select one of three "Levels of unloading": If the clinician wants maximal possible support even at a high risk of suction, he sets the level "high"; if he prefers a support at a more secure level, he sets unloading to "low"; or to "medium".

The control system will attempt to obtain the desired flow set by the physician (either constant or depending on heart rate as described above). If the patient's venous return is not sufficiently high enough to provide this desired flow, the controller will try to pump the maximal possible flow, depending on suction diagnostics and "near-flat line" flow pattern characteristics. In this situation the controller will "decide" on a flow-maximization/suction-minimization balance depending on the "Unloading Level". If the "Unloading Level" is set to low or medium, then a certain peak-to-peak amplitude or peak-to-peak amplitude is maintained if the desired flow rate cannot be achieved. If the "Unloading Level" is set to high, then the speed is no longer increased when a predetermined dQ/dn value (diminishing returns with respect to mean flow) or dP2P/dn (diminishing returns with respect to flow peak-to-peak amplitude) is achieved. If this maximal possible flow falls below the minimal acceptable flow for a predetermined amount of time, the controller will switch to constant speed mode and activate an alarm.

The aforementioned control strategy is believed to cover all usual patient conditions from the early postoperative patient to the recovered patient or to a patient at weaning, illustrated by the following examples:

a) Postoperative patient with weak right heart, maximal unloading desired: The clinician sets the desired flow to a high level, e.g. 8 L/min, and sets Unloading Level high. The pump will run on maximal possible flow if the desired flow cannot be achieved.

b) Old, slightly recovered patient at normal ward, high rest heart rate, moderate heart rate increase at exercise: The heart rate is checked at rest and set (e.g. 90 bpm), and heart rate at acceptable exercise is determined (e.g. 110 bpm, when walking around the bed). The clinician sets the desired flow at rest (e.g. to 4 L/min), and sets the desired flow at exercise (e.g. 6 L/min). The pump will give an exercise-dependent flow, and reduce that flow in case of suction danger to maximal possible flow, for example, if the patient becomes dehydrated.

c) Young, fully recovered, mobile patient with normal heart rate variability: The clinician sets the heart rate at rest (e.g. 65 bpm), and checks heart rate at acceptable exercise, e.g. bicycle training or stair walking (e.g. 130 bpm). flow at rest is set to 4 L/min, and the flow at exercise is set to 7.5 L/min. This setting will provide high reactivity to exercise.

d) Patient at weaning, intentionally reduced support: Desired flow is set to 2 L/min, for example, and the patient's heart should provide the rest of workload.

If the desired flow is set too high, no significant risk occurs, as the pump will always run on maximal flow. If the desired flow is set too low, the same risk occurs as with an open-loop controlled system: the support may be inappropriate, but still be set at a minimal, safe speed, for example, 7.5 krpm. If the heart rate values are set inappropriately, the physiological response may become awkward and be sub-optimal for response to exercise, but it would not likely endanger the patient.

The constant speed mode is especially applicable, for example, if the flow-sensor is defective, or in patients with extreme irregularities in the flow patterns making suction detection difficult. It is also appropriate for candidates when weaning from cardiopulmonary bypass and for patients with a balloon pump or other atypical cannula configurations. The constant speed mode is typically not appropriate for patients with highly variable arterial pressure, patients with highly variable flow demand (e.g. large day-night-variation, causing suction at night and underperfusion during day) and patients who would need maximal possible support.

The flow controlled mode is particularly applicable for patients with somewhat recovered heart function and a limited desire for physical exercise (with parameters set for desired flow depending heart rate) and in patients who are weaning from the assist device (with desired flow set to a low level). The flow controlled mode is useful for early postoperative protection of right heart (to avoid volume overload) and in situations where stable pumping conditions are desired (with desired flow set to a constant level to achieve a given cardiac index). Additionally, the flow controlled mode is suitable for patients requiring maximal support (with desired flow set to a high level, so that control is achieving the "maximal flow" possible), for patients with highly variable arterial pressure and rather unstable compensatory mechanisms, and for patients with variation of circardian rhythm (who would experience, at constant speed, suction during night and too low assistance during daytime). The flow controlled mode is typically not suitable for patients with very atypical suction patterns.

Several factors are considered to determine the maximal flow rate. For example, the following criteria may be used to determine maximal flow rate while avoiding suction:

Peak-to-peak amplitude vs. Speed: Peak-to-peak amplitude (pulsatility) should decrease to a minimum before suction, which minimum however can highly depend on cannula position and ventricular structure.

Speed Increase vs. Flow Increase (dQ/dn): If speed is increased without relevant increase of flow (diminishing returns), an increase of pressure difference without hemodynamic benefit may be assumed.

Power increase vs. speed increase (dPower/dn): If power is increased without sufficient relevance to flow, this indicates an increased hydraulic loss within the pump system (may require normalization for power, i.e. (dPower/dn)/Power).

From the regression curves, a proposed speed change and maximal possible flow are calculated as disclosed below. As noted above, varying levels of Unloading Levels may be employed, assuming that the risk for suction is greater with the greater the unloading.

If the Unloading Level is set "Low":

a) Determination of desired peak-to-peak amplitude value:
Set desired-peak-to-peak amplitude to a predetermined value, for example 2.5 L/min;
If dPower/dn>Critical Value, then increase desired-peak-to-peak amplitude-to a predetermined value, for example 0.5 L/min;
If dQ/dn<Critical Value, then increase desired-peak-to-peak amplitude to a predetermined value, for example 0.5 L/min;

b) Reaction to eventual Suction or increasing of peak-to-peak amplitude with increasing speed:
If suction has occurred within the last two minutes, then increase desired peak-to-peak amplitude to a predetermined value, for example 0.5 L/min. (Note: A suction event additionally causes the reduction of speed for predetermined time period by a predetermined amount depending on the certainty of suction).
Determine flank of peak-to-peak amplitude vs. speed by speed variation (10 secs increase 150 RPM, 10 secs decrease 150 RPM): If the working point is in the rising flank of the peak-to-peak amplitude vs. speed diagram, then reduce speed c) Regular mode: Control of peak-to-peak amplitude:
If the working point is in the falling flank, and no suction had recently occurred, then adjust to desired peak-to-peak amplitude value by a Proportional-Integral (PI) controller If the Unloading Level is set "Medium" (same strategy as "low", but with modified parameters):
Initial desired peak-to-peak amplitude value 1.5 L/min
Speed decrease in case of suction 100-300 rpm per event per second
In case of increasing peak-to-peak amplitude flank speed change 50 rpm/10 secs If the Unloading Level is set "High" and desired flow cannot be achieved, flow is maximized by a predetermined value of diminishing return for mean flow (dQ/dn), a predetermined value of peak-to-peak amplitude, CIW, which is usually the speed where peak-to-peak amplitude is minimized, or by a predetermined value of pump power over pump speed, dPower/dn.:

a) Determine critical increase of peak-to-peak amplitude:
Set CIW (i.e. critical increase of peak-to-peak amplitude) to given constant. This is the threshold value for peak-to-peak amplitude.
If dQ/dn is lower than the critical level of dQ/dn, then increase CIW
If dPower/dn higher then critical level of dPower/dn, then increase CIW b) Reaction to a Suction event:
If suction has occurred within the last (2) min, then decrease CIW (Note: A suction event additionally causes the reduction of speed for a predetermined time period by a predetermined amount depending on the certainty of suction.)

c) Find borderline speed to adjust to CIW in a stepwise fashion:
Increase speed by predetermined amount, calculate dpeak-to-peak amplitude/dspeed;
If new dpeak-to-peak amplitude/dspeed<CIW then increase speed further,
else i.e. critical CIW already reached): go back one step and check the step before,
if now above CIW:
if still above CIW, reduce speed further,
else try to increase speed again.

In FIGS. 7-12, six flowcharts for flow control routines are shown. From these six routines, routine 1 (FIG. 7) is called as an interrupt routine by each suction event. Routine 2 (speed variation) (FIG. 8) is called by routine 3 (FIG. 9) after a defined control time. The remaining routines are called every 10 milliseconds. They communicate with each other by variables, markers and timers. Therefore, the sequence of their calculation makes no difference. Depending on the chosen sensitivity, not all of them need necessarily to be calculated every time, but for transition purposes at switchover this may be preferable.

Figure 7:
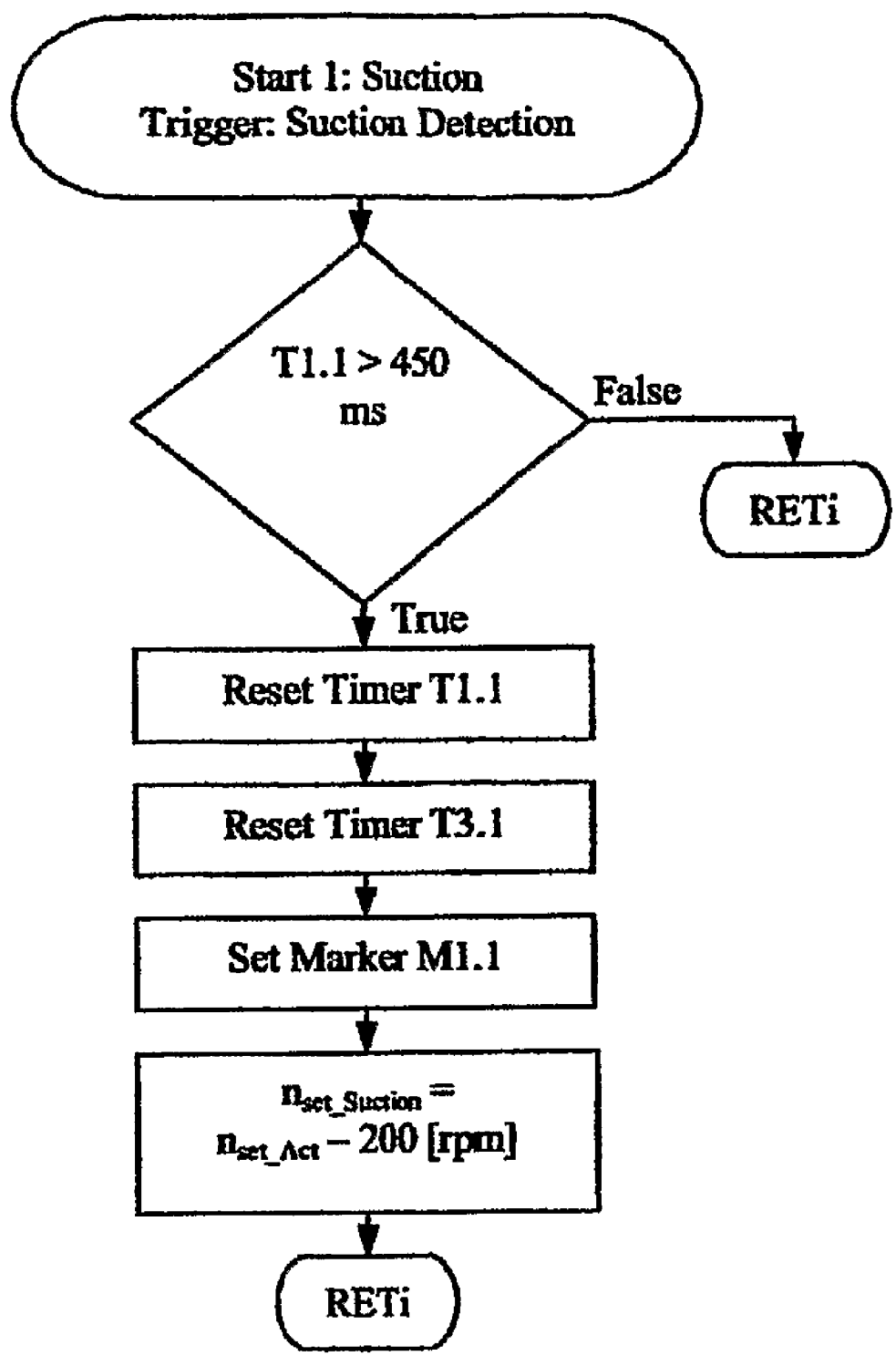
FIGS. 7-12 are flow diagrams illustrating flow control routines in accordance with aspects of the present invention.

The suction subroutine, shown in FIG. 7, is triggered by each new arising suction condition. The routine itself takes care not to react multiple times to the same suction cycle, by checking a timer T1.1. Timer T1.1. is started in the initiating routine and then reset by every accepted suction. A suction event is accepted if the last suction has occurred earlier then 450 msecs before. After a suction event, the flow control subroutine (FIG. 9) stays 15 seconds at a reduced speed level, which time period is also controlled by Timer T1.1.

A Timer T3.1 is responsible for speed variation. A suction event stops an eventual speed variation and takes care, that the next speed variation does not start too early.

A Marker M1.1 is responsible for adaptation of currently unused controllers to the actual value by keeping the integrators valid (follow up-function, necessary if control loop is open). Each accepted suction causes a speed reduction of 200 rpm.

Figure 8A:
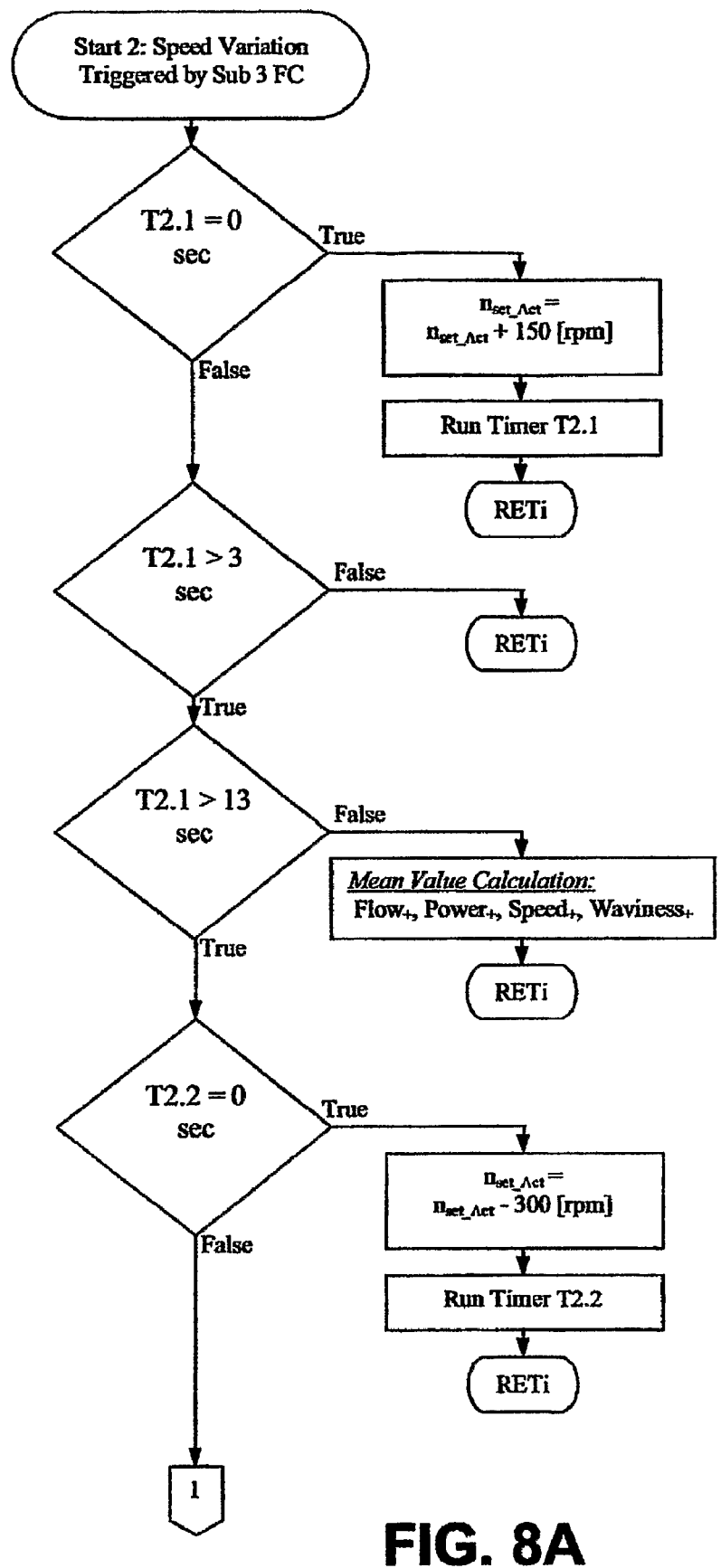
Figure 8B:
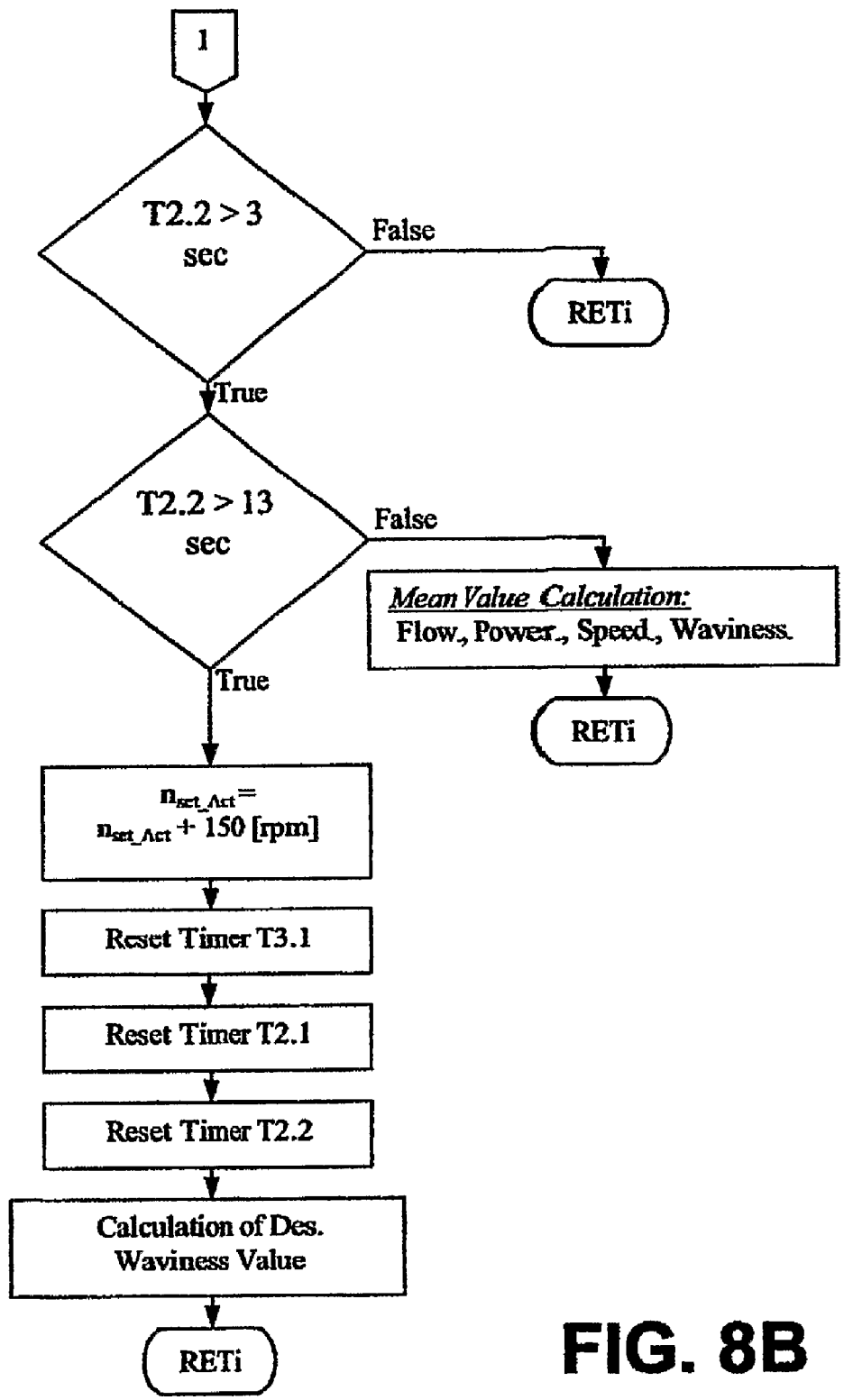

The subroutine speed variation shown in FIGS. 8A and 8B is called by the main subroutine Flow Control (FIG. 9) after a predefined time period to cause a speed increase and a following speed decrease around the working point. It increases speed for 150 rpm for 13 seconds and measures values after a transition period of 3 secs, and then decreases for 300 rpm (150 from the initial value). For timing reasons this step could also be done as a single decrease using the data of the control period as a second data point.

Timers T2.1 and T2.2 are responsible for the 3 and 13 second intervals, respectively. A shorter data collection period than 10 seconds may be possible to shorten the non-regulated time.

Following data collection at the decreased speed level, the system returns to the speed previously used at control. Timers T3.1, T2.1 and T2.2 are reset. Timer T3.1 is responsible for the next call of the speed variation routine, and Timers T2.1 and T2.2 are responsible for each up- and down-speed variation. Finally, the Desired-Peak-to-peak amplitude-Value is calculated as noted above, depending on the chosen unloading level (low or medium).

Figure 9A:
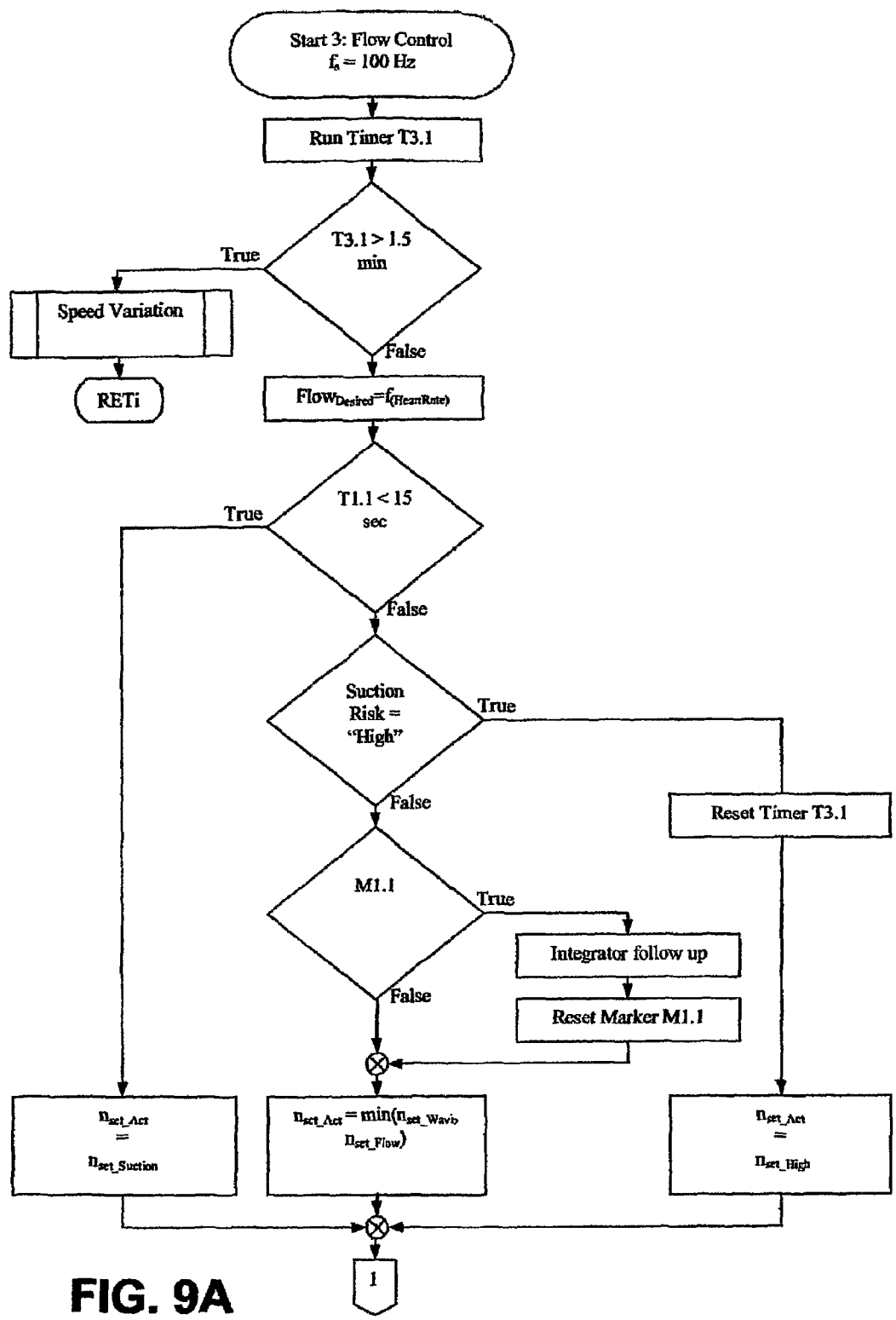
Figure 9B:
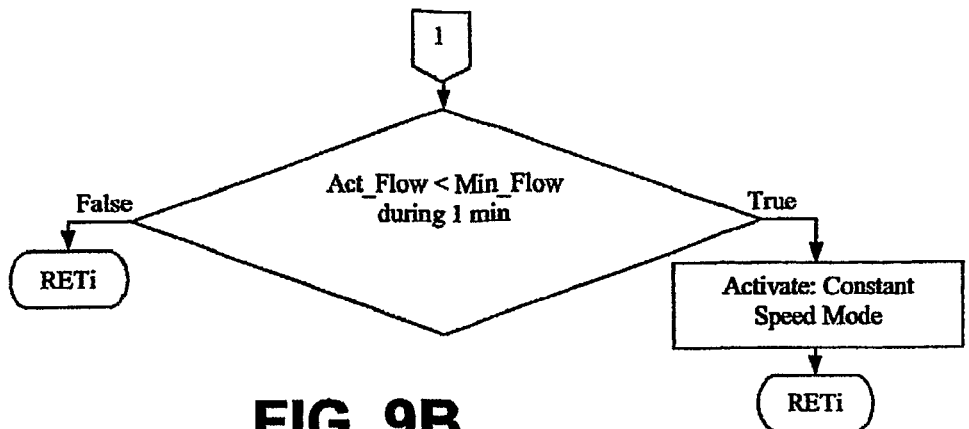

FIGS. 9A and 9B illustrate the Main Flow control routine, which decides on the control mode actually used (which could depend on the three suction sensitivity levels, a speed variation from time to time, or a permanent switchover to constant speed in case of persistent low flow). Timer T3.1 determines how often a speed variation for the calculation of the desired-peak-to-peak amplitude-value is performed (set to 1.5 minutes control time in one implementation). Timer T3.1 is not active in case of "high unloading" i.e. minimum control. Timer T1.1 takes care, that after a suction event, a constant reduced speed is run for 15 seconds.

If high unloading level is requested, then no speed variation (triggered by Timer 3.1) is needed. M1.1 is set in case of suction, or in the high unloading level, then and only then a follow up of the peak-to-peak amplitude and desired speed controller is required. In case of low flow for more than 1 minute, a switchover to constant speed mode is generated.

Figure 10:
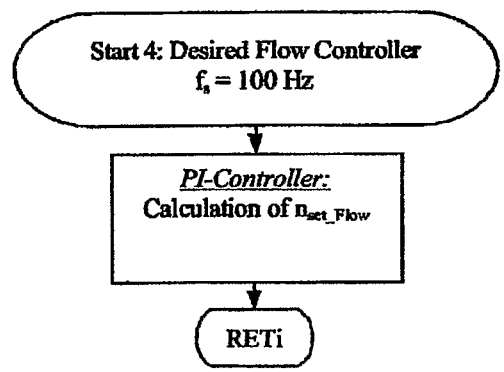
Figure 11:
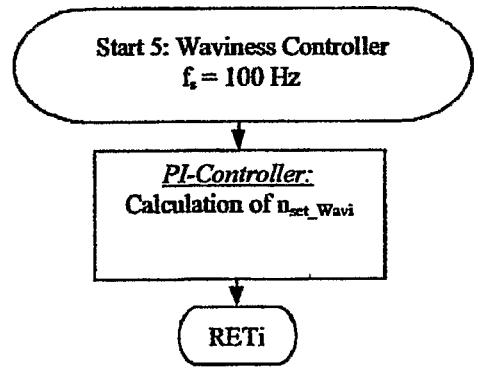

FIG. 10 shows the subroutine for calculation of the speed adaption for the desired flow mode as a conventional PI-controller. FIG. 11 illustrates the subroutine for calculation of the speed adaptation for peak-to-peak amplitude control, taking the actual peak-to-peak amplitude as the control variable. Both subroutines 4 and 5, shown in FIGS. 10 and 11, respectively, are deactivated after suction events for 15 seconds and for the time of a speed variation. During these actions, however, the calculation is continued in the background and the integrators are kept in a follow up mode to guarantee a smooth switchover if necessary.

Figure 12:
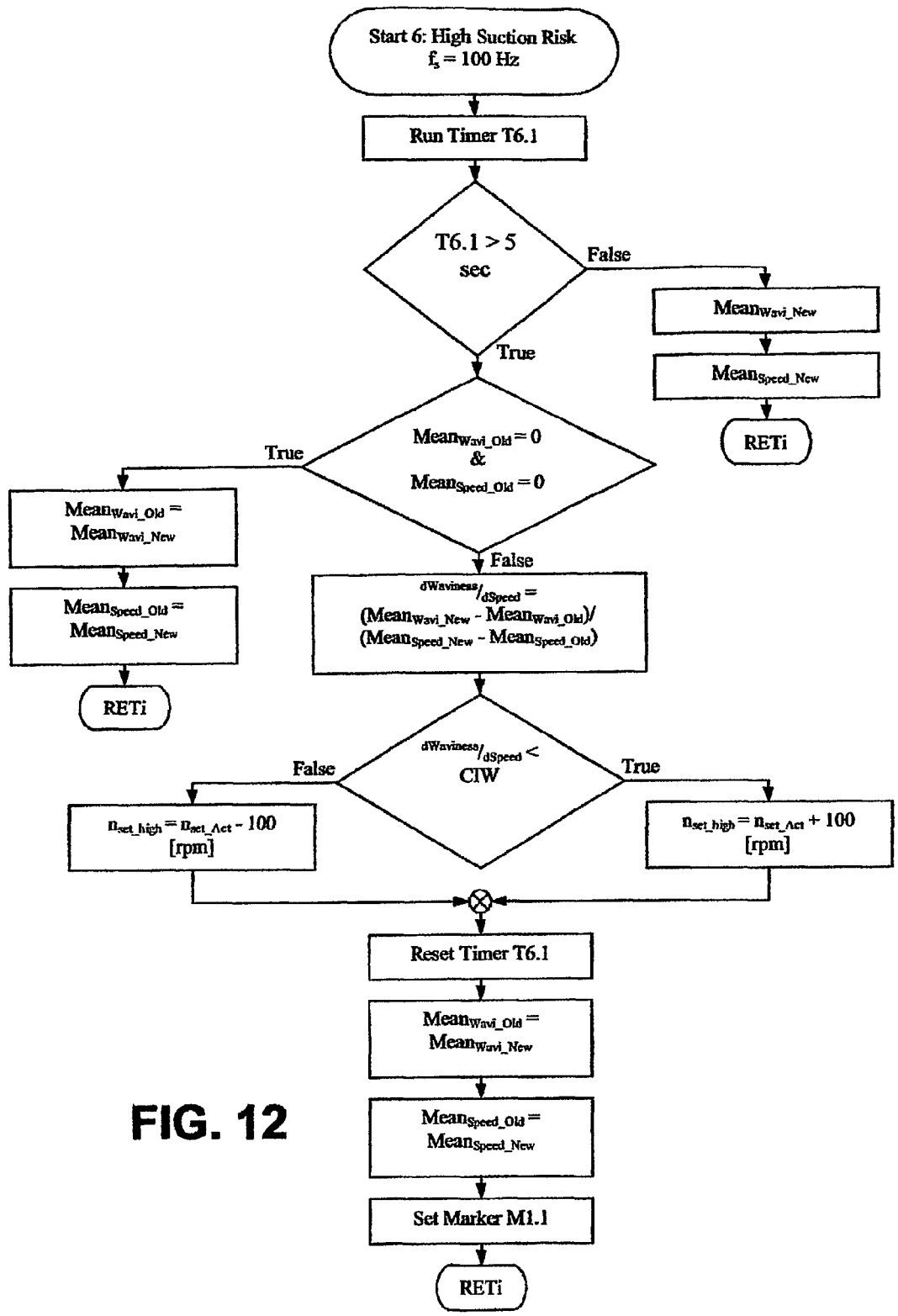

FIG. 12 illustrates the subroutine for evaluation of minimal peak-to-peak amplitude, accepting a high risk of suction. Timer 6.1 is used for mean value calculation of peak-to-peak amplitude and speed (set for 5 seconds in one implementation). At the first entry the historical mean values are set equal to the actual values. The dW/dn is determined and the decision is made whether speed has to be increased or decreased in the following step. Timer T6.1 is reset for the next mean value calculation, and measured data is shifted for the next calculation. Marker M1.1 is set to show that the controllers on peak-to-peak amplitude and on desired flow were not active in this cycle.

In an exemplary implementation, for optimization of the working point concerning minimization of potential suction and to optimize pump efficiency and blood protection, the desired P2P-Flow-Amplitude (dP2PFA) can be adapted either manually (such as done by setting of medium or low unloading) and/or with automatic adaptation. For this automatic adaptation, the data derived from speed variation are used. Depending on the increment respectively decrement of flow and the percentage of input power a decision about increasing or decreasing the dP2PFA is made.

Figure 13:
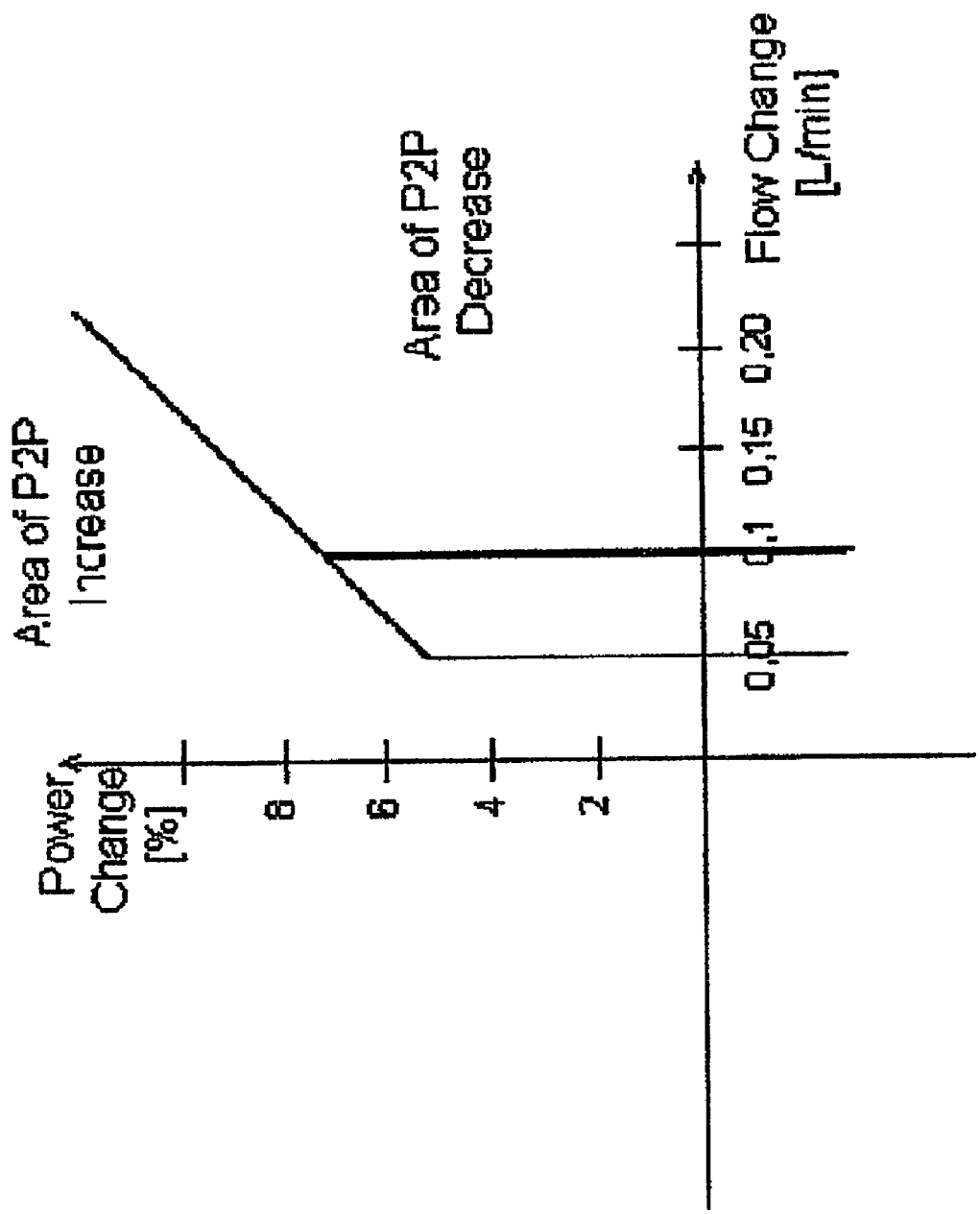
FIGS. 13 and 14 are characteristic curves for determination of desired peak to peak flow amplitude.

FIG. 13 shows a typical example of a characteristic curve for such increase or decrease: Depending on flow change and percentage power change due to the speed variation, the working point in the plane is determined.

If at such speed increment the flow increases less then a certain amount (for example less than 0.05 L/min at a speed increase of 200 rpm) or even decreases, or if the power required for a moderate increase is comparably high (in the given example more than 10% power increase for a flow increase of only 0.1 L/min, 15% power increase for 0.15 L/min and linearly extrapolated), or if the dP2PFA is less than −0.05 L/min at this given speed increase, then dP2PFA is increased for 0.025 L/min, because the system assumes that a higher dP2PFA would lead to less power consumption.

If at such speed increment the flow increases more then a certain amount (for example more than 0.1 L/min at a speed increase of 200 rpm), and if the power increase required for that increase is comparably low (in the given example less than 10% power increase for a flow increase of 0.1 L/min, less then 15% power increase for 0.15 L/min and linearly extrapolated), or if the dP2PFA is less than −0.05 L/min at this given speed increase, then dP2PFA is increased for 0.025 L/min, because the system assumes that a higher dP2PFA would lead to less power consumption.

If at such speed increment the flow does increase in the expected range (for example between 0.05 to 0.1 L/min) and the power does not increase excessively (for example less than 5 to 10%, then the dP2PFA should be kept unchanged.

These borders, for which typical numbers are given in the description above and in FIG. 13, may be either set stable or be allowed to modified by the clinician. A shift of these borders to the left side, that is lower flow triggers, would result in a more aggressive pumping at a price of higher power and a higher risk of suction. Setting the borders to higher flow levels would result in even more cautious pump setting, sparing power and decrease the risk of suction, but for the price of less unloading of the supported heart.

Figure 14:
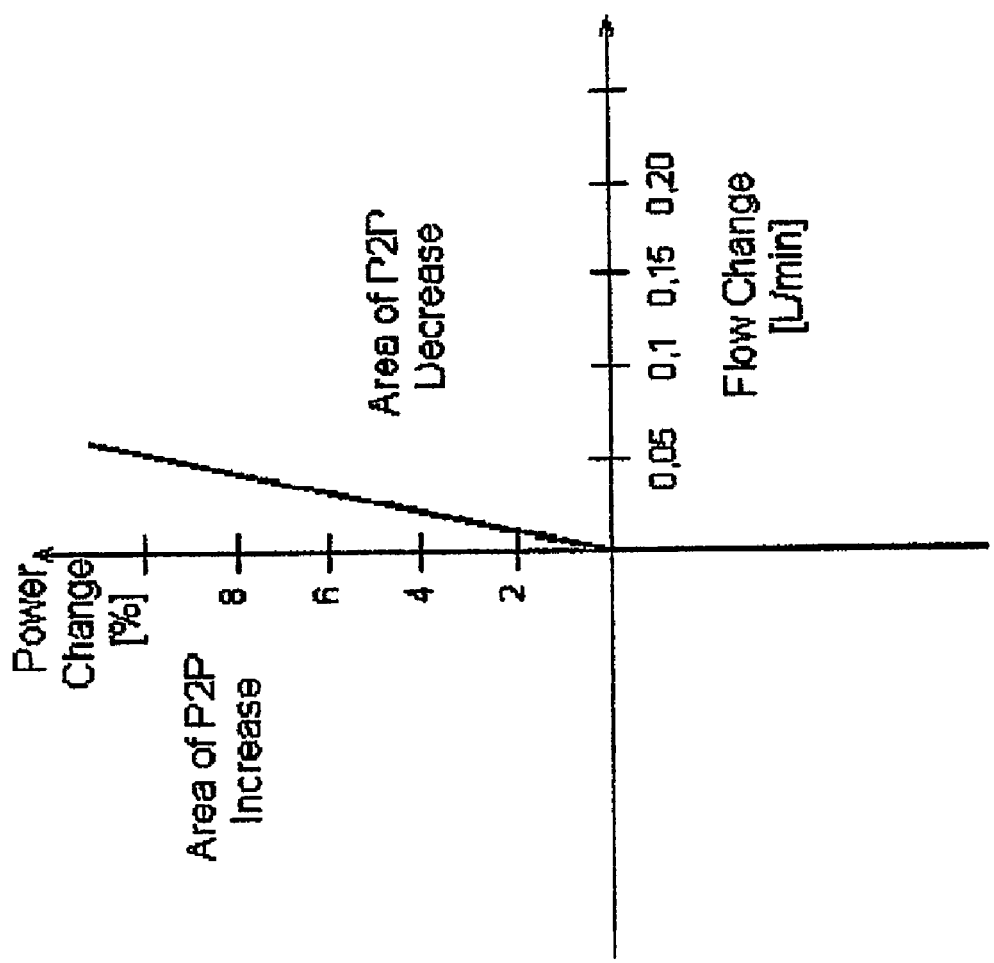

In a simplified version, the setting may even be changed to one single discrimination line (see FIG. 14). In this simplified version:

dP2PFA is increased, if flow and power decrease at a speed increase or flow increases only very slightly with a concurrent power increase (for example less than 0.05 L/min flow increase at a power increase of more than 5%, or proportional), or if dP2PFA decreases for values below −0.2 L/min;

dP2PFA is decreased, if flow increases at a speed increase and power does not increase more than per 5% for an increase of 0.05 L/min.

This setting leads to a rather aggressive unloading strategy, also for the price of a considerable elevated pump power.

Modified parameters may be employed. For example, instead of a percentage definition of power change, a definition of a power increase in absolute numbers could be used, and similarly, instead of a flow definition via absolute numbers a percentage description could be used.

Further, instead of a linear definition of the border, a definition of the border via a nonlinear function (for example a square root function or similar) could be used. Still further, instead of a distinct binary decision, a smooth transition could be used, which could either be defined via a function or by a fuzzy logic set.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of controlling a blood pump, comprising:
monitoring a blood flow;
monitoring a pump power;
calculating a desired peak to peak flow amplitude in response to predetermined system parameters, wherein calculating the desired peak to peak flow amplitude includes temporarily increasing the pump speed and either—
increasing the desired peak to peak flow amplitude if the flow increases less than a predetermined amount in response to the increased pump speed, or
increasing the desired peak to peak flow amplitude if the power increases more than a predetermined amount in response to the increased pump speed.

2. The method of claim 1, further comprising monitoring a flow rate change corresponding to the temporary pump speed.

3. The method of claim 1, further comprising monitoring a power change corresponding to the temporary pump speed.

4. The method of claim 1, further comprising increasing the desired peak to peak flow amplitude if the flow increases less than a predetermined amount in response to the increased pump speed.

5. The method of claim 1, further comprising increasing the desired peak to peak flow amplitude if the power increases more than a predetermined amount in response to the increased pump speed.

6. The method of claim 1, further comprising increasing the desired peak to peak flow amplitude if the flow increases more than a predetermined amount and the power increases less than a predetermined amount in response to the increased pump speed.

7. The method of claim 1, further comprising decreasing the desired peak to peak flow amplitude if the flow increases and power does not increase more than a predetermined amount in response to the increased pump speed.

8. A blood pump system, comprising:
a pump; and
a controller coupled to the pump, the controller monitoring blood flow and operating the pump to achieve a desired peak to peak flow amplitude, wherein the controller increases the desired peak to peak flow amplitude if the flow increases less than a predetermined amount in response to a temporary increase in pump speed.

9. The system of claim 8, wherein the controller also monitors pump power and increases the desired peak to peak flow amplitude if the power increases more than a predetermined amount in response to the increased pump speed.

10. The system of claim 8, wherein the controller also monitors pump power and increases the desired peak to peak flow amplitude if the flow increases more than a predetermined amount and the power increases less than a predetermined amount in response to the increased pump speed.

11. The system of claim 8, wherein the controller also monitors pump power and decreases the desired peak to peak flow amplitude if the flow increases and power does not increase more than a predetermined amount in response to the increased pump speed.

12. A blood pump system, comprising:
a pump; and
a controller coupled to the pump, the controller monitoring pump power and operating the pump to achieve a desired peak to peak flow amplitude, wherein the controller increases the desired peak to peak flow amplitude if the power increases more than a predetermined amount in response to a temporary increase in pump speed.

13. The system of claim 12, wherein the controller also monitors blood flow and increases the desired peak to peak flow amplitude if the flow increases more than a predetermined amount and the power increases less than a predetermined amount in response to the increased pump speed.

14. The system of claim 12, wherein the controller also monitors blood flow and decreases the desired peak to peak flow amplitude if the flow increases and power does not increase more than a predetermined amount in response to the increased pump speed.

* * * * *